US011035979B2

(12) United States Patent
Hahn

(10) Patent No.: US 11,035,979 B2
(45) Date of Patent: Jun. 15, 2021

(54) VISUAL BIOFEEDBACK APPARATUS

(71) Applicant: Christopher James Hahn, Longmont, CO (US)

(72) Inventor: Christopher James Hahn, Longmont, CO (US)

( * ) Notice: Subject to any disclaimer, the term of this patent is extended or adjusted under 35 U.S.C. 154(b) by 106 days.

(21) Appl. No.: 16/592,597

(22) Filed: Oct. 3, 2019

(65) Prior Publication Data
US 2020/0033499 A1    Jan. 30, 2020

Related U.S. Application Data

(60) Provisional application No. 62/742,489, filed on Oct. 8, 2018.

(51) Int. Cl.
| | | |
|---|---|---|
| G01V 8/20 | (2006.01) | |
| A61B 5/00 | (2006.01) | |
| A63B 24/00 | (2006.01) | |

(52) U.S. Cl.
CPC ............... *G01V 8/20* (2013.01); *A61B 5/486* (2013.01); *A63B 2024/0012* (2013.01); *A63B 2220/803* (2013.01)

(58) Field of Classification Search
CPC ............ A61B 5/486; A63B 2024/0012; A63B 2220/803
See application file for complete search history.

(56) References Cited

U.S. PATENT DOCUMENTS

| | | | |
|---|---|---|---|
| 4,293,814 A | 10/1981 | Boyer | |
| 4,717,864 A | 1/1988 | Fultz | |
| 5,285,154 A | 2/1994 | Burreson | |
| 5,705,924 A | 1/1998 | Jeffers | |
| 5,986,450 A | 11/1999 | Haigh et al. | |
| 6,002,350 A | 12/1999 | Checa et al. | |
| 6,829,952 B2 | 12/2004 | Stanley et al. | |
| 6,843,143 B2 | 1/2005 | Steele et al. | |
| 7,082,823 B1 | 8/2006 | Shipman et al. | |
| 7,301,334 B2 | 11/2007 | Shen et al. | |
| 7,602,271 B2 | 10/2009 | York et al. | |
| 7,764,154 B2 | 7/2010 | York et al. | |
| 7,777,482 B2 | 8/2010 | Munz et al. | |
| 7,876,186 B2 | 1/2011 | York et al. | |
| 8,120,351 B2 | 2/2012 | Rettig et al. | |
| 8,801,361 B2 | 8/2014 | Hawkins | |
| 9,933,323 B2 | 4/2018 | Schweizer et al. | |
| 10,012,518 B2 | 7/2018 | David et al. | |
| 2004/0122334 A1 | 6/2004 | Yamashiro | |
| 2008/0225520 A1* | 9/2008 | Garbus | G01J 3/462 362/231 |

(Continued)

*Primary Examiner* — Thanh Luu
*Assistant Examiner* — Monica T Taba
(74) *Attorney, Agent, or Firm* — Thomas J. Lavan

(57) ABSTRACT

A device is provided. The device includes one or more of a plurality of sensor/light source groups, each including a sensor, a first light source of a first color, and a second light source of a second color, arranged in sequence along an expected direction of travel of an object. The device also includes a device to track objects, coupled to the plurality of sensor/light source groups, and configured to drive first light sources in response to playback of a stored sequence and drive second light sources in response to received active sensor outputs from sensors of the plurality of sensor/light source groups.

19 Claims, 7 Drawing Sheets

(56) References Cited

U.S. PATENT DOCUMENTS

| | | | |
|---|---|---|---|
| 2013/0093335 A1* | 4/2013 | Vinkenvleugel | H05B 47/10 |
| | | | 315/158 |
| 2014/0266159 A1 | 9/2014 | Heremans et al. | |
| 2017/0284829 A1 | 10/2017 | Cai et al. | |
| 2018/0031628 A1 | 2/2018 | Ahrens et al. | |
| 2019/0091537 A1* | 3/2019 | D'Alesio | A61B 5/1112 |
| 2019/0332838 A1* | 10/2019 | Vancorenland | G06K 7/1417 |

* cited by examiner

Fig. 1A Object Tracking System
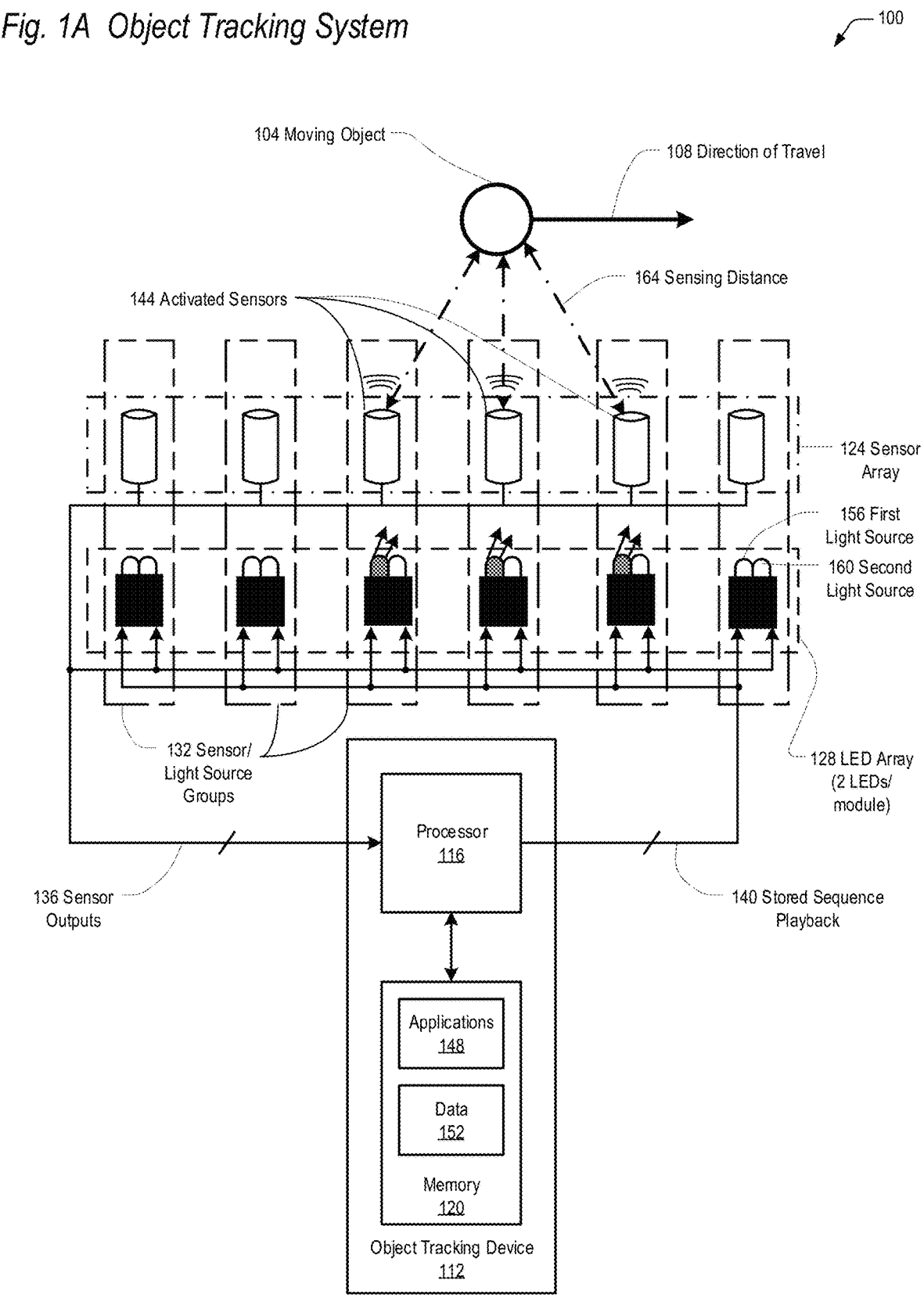

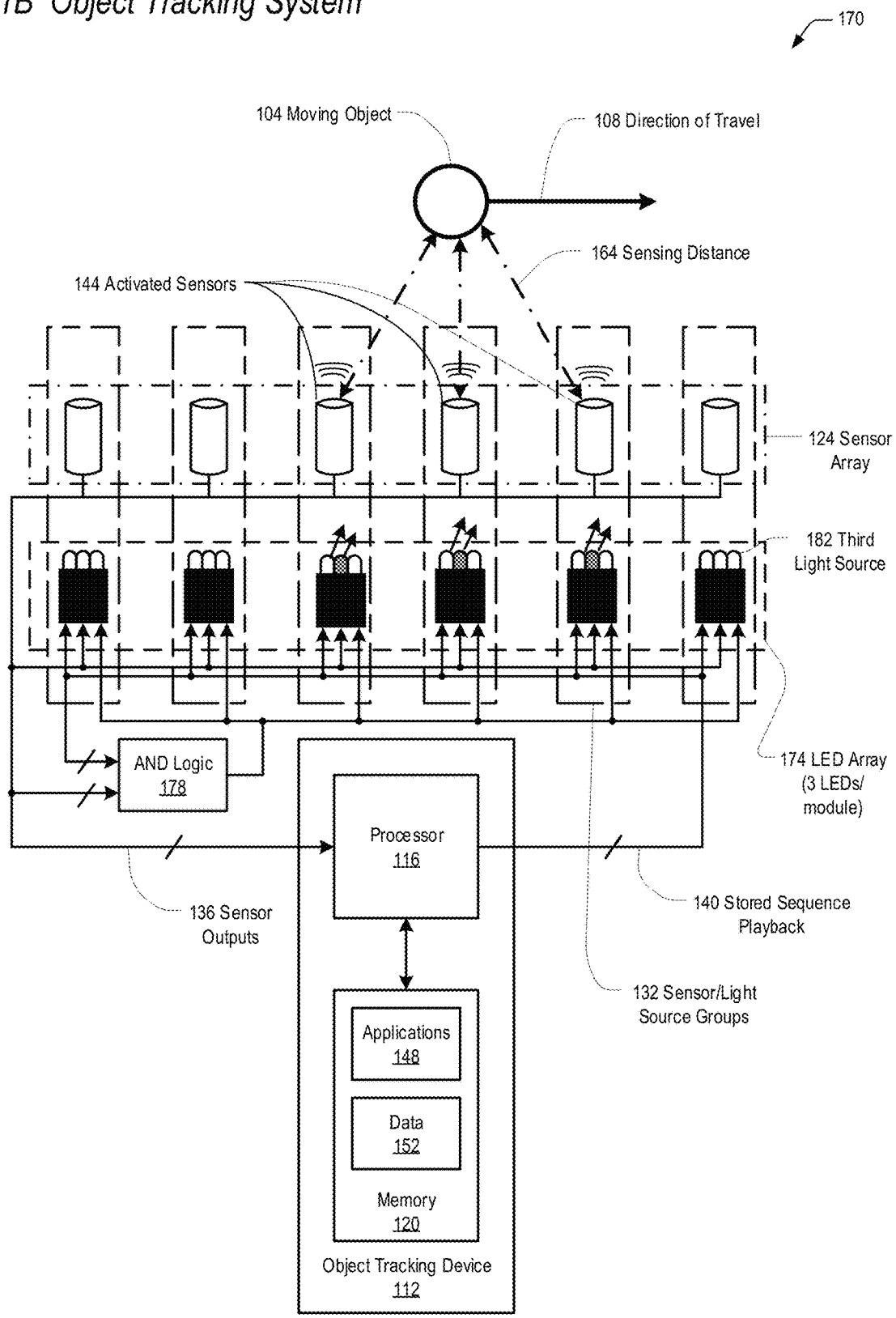
Fig. 1B Object Tracking System

*Fig. 2A  LED Activation based on 2 LEDs/Module*
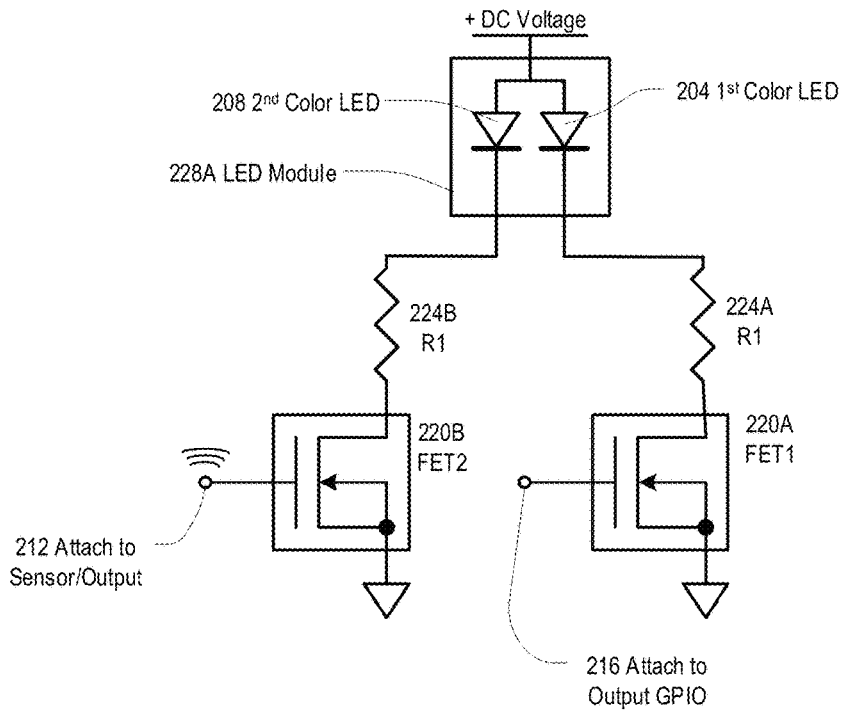
*Fig. 2B  LED Activation based on 3 LEDs/Module*
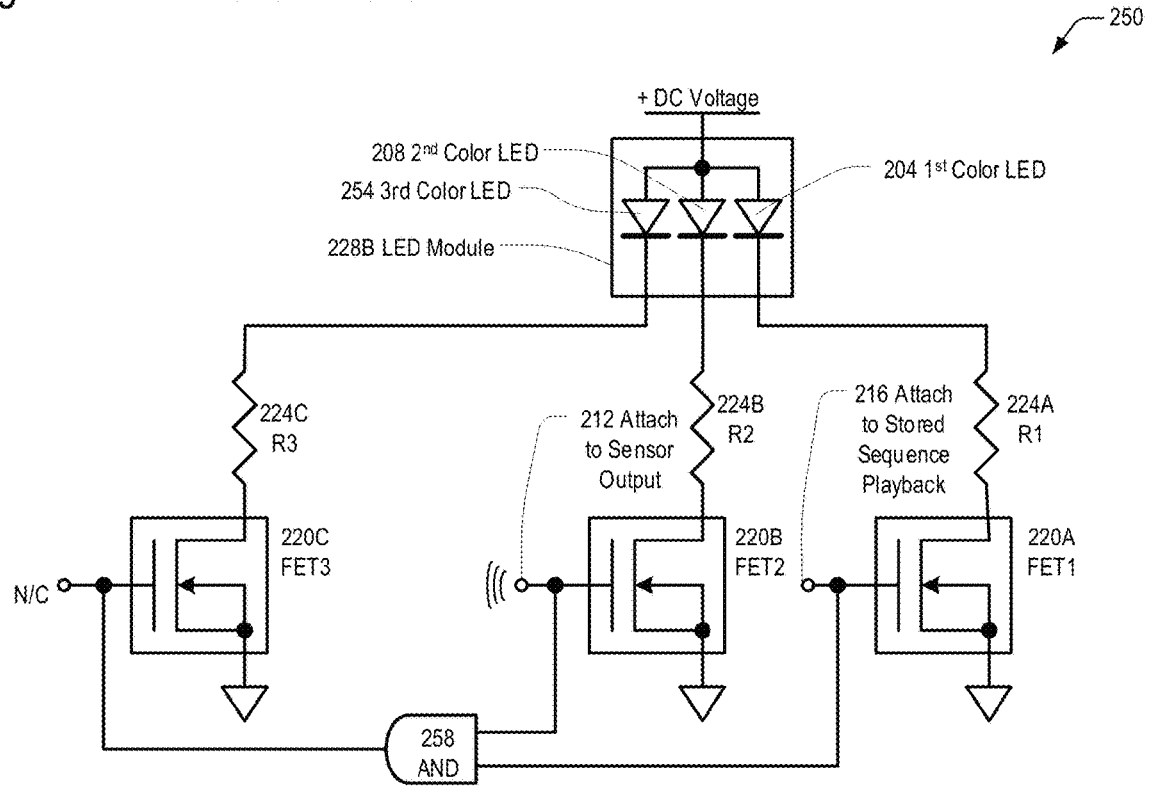

Fig. 3 Stored Sequence
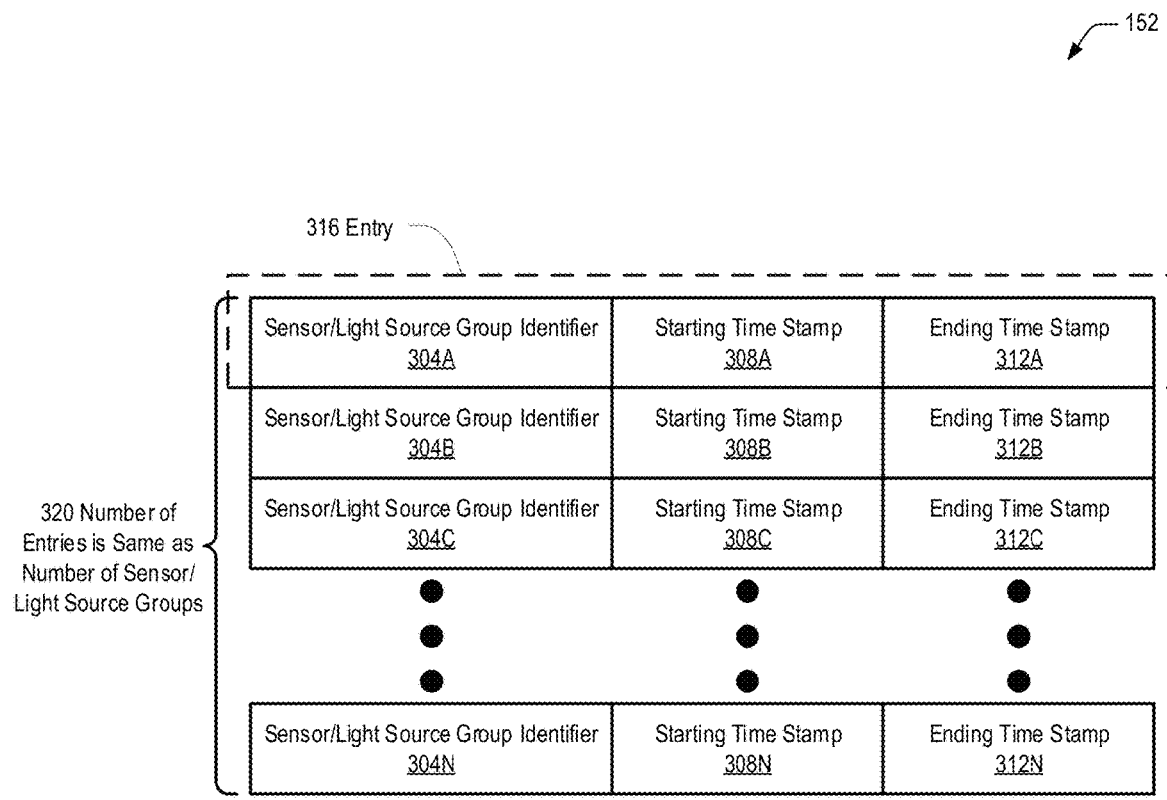

*Fig. 4A Object Movement Lags Recorded Sequence*
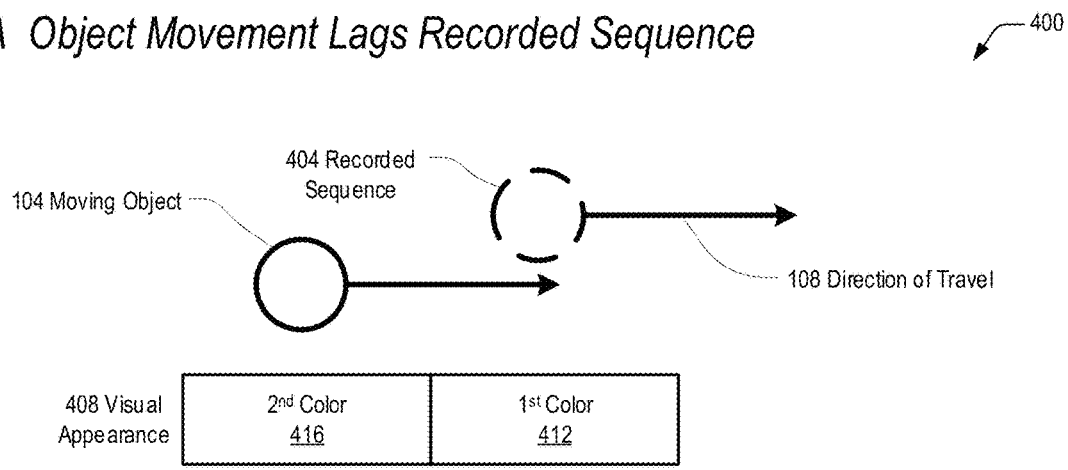
*Fig. 4B Object Movement Leads Recorded Sequence*
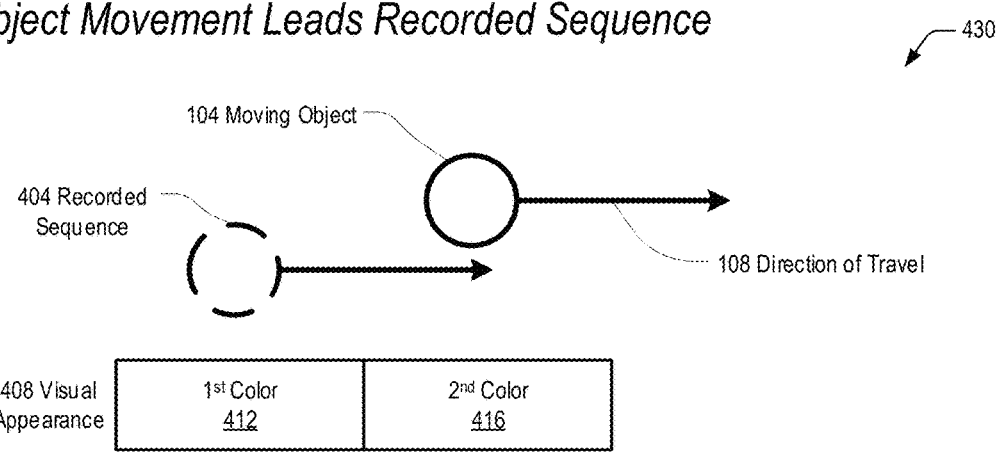
*Fig. 4C Object Movement Matches Recorded Sequence*
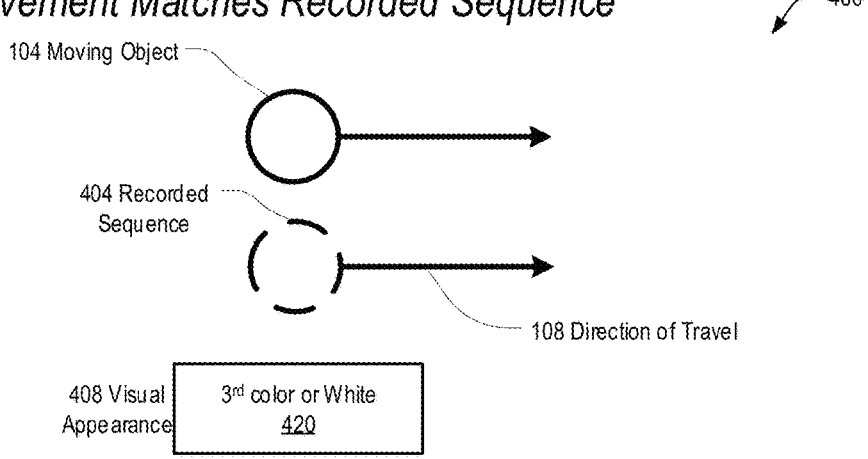

*Fig. 5A Initialization Method for Object Movement*
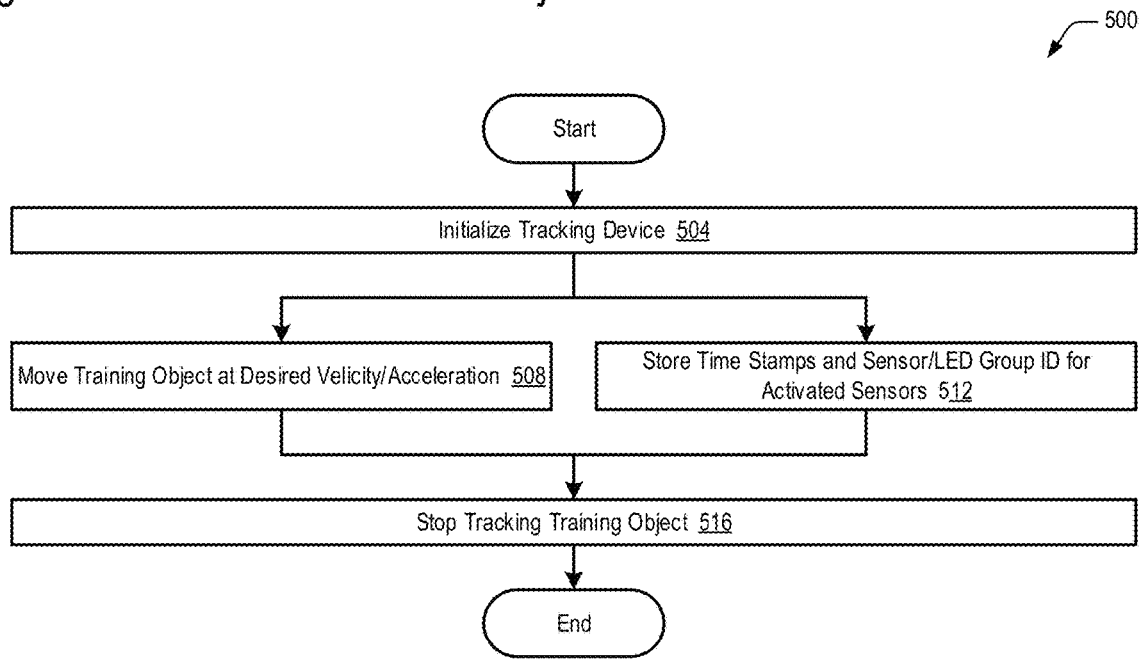
*Fig. 5B Time Stamp Generation Based on Sensors*
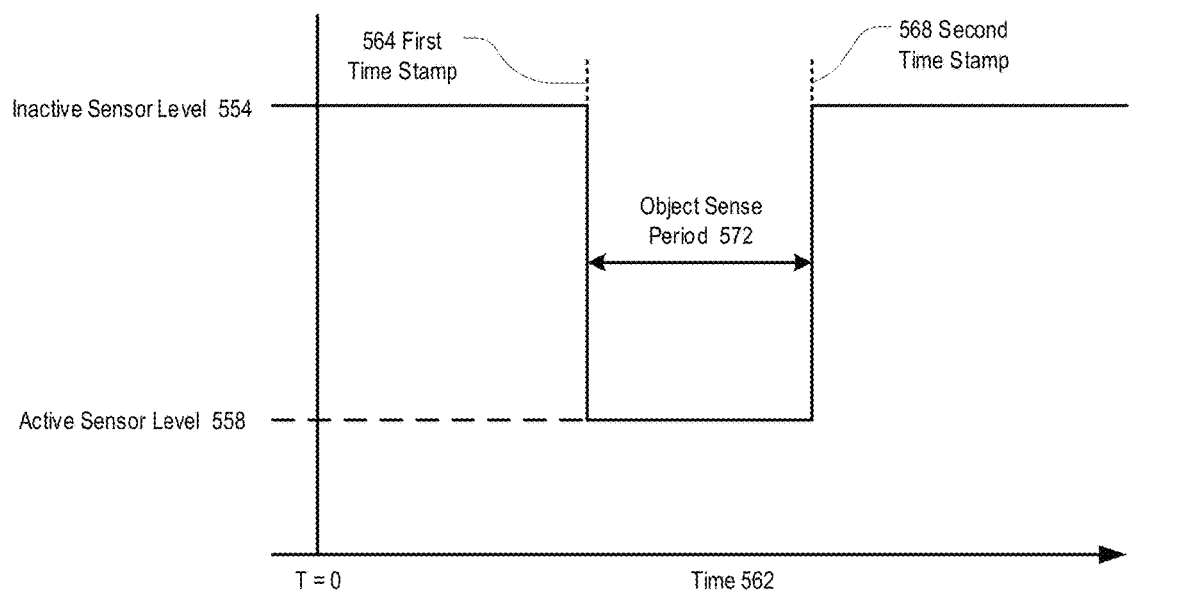

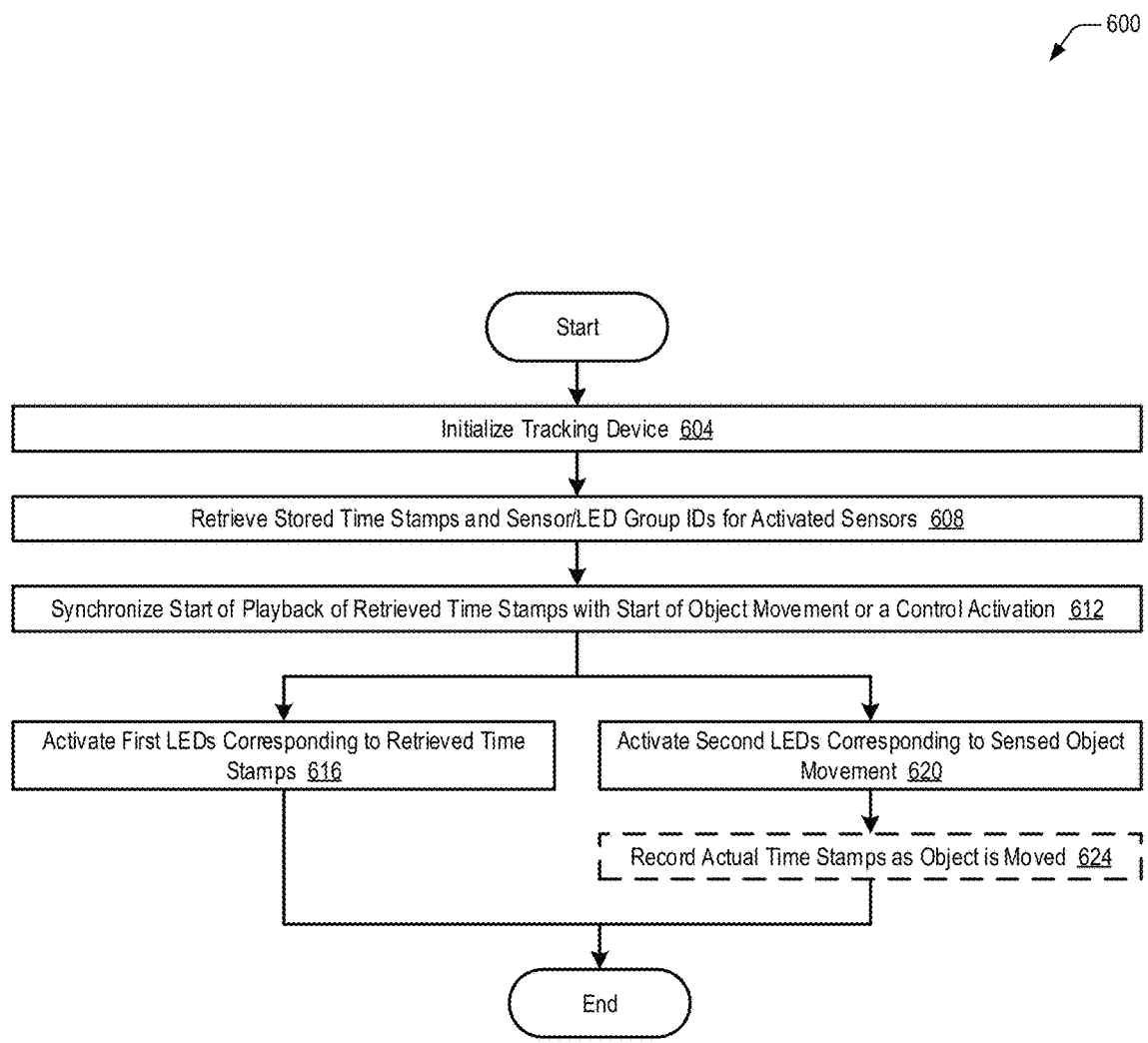
Fig. 6 Training Method for Object Movement

VISUAL BIOFEEDBACK APPARATUS

CROSS REFERENCE TO RELATED APPLICATION(S)

This application claims priority to earlier filed provisional application No. 62/742,489 filed Oct. 8, 2018 and entitled "LED VISUAL BIOFEEDBACK METHOD", the entire contents of which are hereby incorporated by reference.

FIELD

The present application is directed to devices and method for sensing object movement. In particular, the present application is directed to methods and apparatuses for using visual biofeedback based on sensed object movement.

BACKGROUND

Conventional position & proximity sensing technologies require benign environments—and/or transmitter/receiver pairs (photo sensors, for example). Such techniques may be constrained to pass the object between two parallel elements, such as, a receiver/transmitter pair. Several types of sensors have traditionally been used for various forms of object detection, including optical sensors, color sensors, touch sensors, ultrasonic sensors, infrared sensors, and Sonar and laser sensors.

Light sensors may be included in the proximity sensor category, and are simple sensors that change the voltage of photoresistors or photovoltaic cells in accordance with the amount of light detected. Light sensors may be, for example, used in very popular applications for autonomous robots that track a marked path.

With color sensors, different colors are reflected with different intensity, for example, an orange color reflects red light in an amount greater than a green color. Color sensors are in the same general category as light sensors, but with a few extra features that can be useful for applications where it is necessary to detect the presence of an object with a certain color or to detect the types of objects on surfaces.

Touch sensors may be included in the proximity sensors category and are designed to sense objects at a small distance with or without direct contact. These sensors are designed to detect changes in capacitance between the onboard electrodes and an object.

Ultrasonic sensors are designed to generate high frequency sound waves and receive an echo reflected by an object. These sensors are used in a wide range of applications and are very useful when it is not important to detect colors, surface textures, or transparency. Ultrasonic sensors may have the following advantages: the output value is linear with the distance between the sensor and the target, the sensor response is not dependent on the colors, transparency of objects, optical reflection properties, or by the surface texture of the object, they are designed for contact-free detection, sensors with digital (ON/OFF) outputs have excellent repeat sensing accuracy, they provide accurate detection of even small objects, and they may work in critical conditions such as dirt and dust. However, ultrasonic sensors may have the following disadvantages: they must view a high density surface for good results (e.g., a soft surface such as foam and cloth has low density and may absorb sound waves emitted by the sensor, they could experience false detection if some loud noises are received, they have a response time slightly less than other types of sensors, they have a minimum sensing distance, and some changes in the environment may affect the response of the sensor (temperature, humidity, pressure, etc.).

Infrared sensors measure infrared (IR) light that is transmitted in the environment to find objects by an IR light-emitting diode (LED). This type of sensor is very popular in navigation for object avoidance, distance measurements, or line following applications. IR sensors are very sensitive to IR lights and sunlight, which makes them useful for applications requiring great precision in spaces with low light. IR sensors may have the following advantages: they may detect infrared light over large areas, they may operate in real-time, they use non-visible light for detection, and they are inexpensive. Disadvantages of IR sensors is they are inherently very sensitive to IR lights and sunlight while be weak in sensing objects of darker colors such as black.

Sonar sensors maybe used primarily in navigation for object detection, even for small objects. These sensors have high performance on the ground and in water. Laser sensors may be very useful for tracking and detection targets located at a long distances. The distance between sensor and target is measured by calculating the speed of light and the time to receive a return. Laser sensors are very precise in measurement.

SUMMARY

The present application is directed to solving disadvantages of the prior art. In accordance with embodiments of the present application, a device is provided. The device includes one or more of a plurality of sensor/light source groups, each including a sensor, a first light source of a first color, and a second light source of a second color, and arranged in sequence along an expected direction of travel of an object. The device also includes a device to track objects, coupled to the plurality of sensor/light source groups, and configured to drive first light sources in response to playback of a stored sequence and drive second light sources in response to received active sensor outputs from sensors of the plurality of sensor/light source groups.

In accordance with another embodiment of the present application, a system is provided. The system includes one or more of an object in motion, a plurality of sensor/light source groups, each including a sensor, a first light source in a first color, and a second light source in a second color. The system also includes a device to track objects, coupled to the plurality of sensor/light source groups. The device to track objects includes a processor and a memory, coupled to the processor. The memory may include instructions and a stored sequence. the processor may be configured to execute the instructions to drive first light sources in response to playback of the stored sequence and in some embodiments drive second light sources in response to received active sensor outputs from sensors of the plurality of sensor/light source groups. In other embodiments, the sensors mat drive the second light sources without processor involvement.

In accordance with yet another embodiment of the present application, a method is provided. The method includes one or more of initiating playback of a stored sequence controlling timed sequential illumination of first light sources of a plurality of sensor/light source groups, illuminating first light sources as directed by playback of the stored sequence, detecting motion of the object by one or more sensors, illuminating second light sources in response to corresponding sensors of the one or more sensors detecting the object, and detecting a third color in response to illuminating the first and second light sources in one or more sensor/light source groups. Each sensor/light source group includes a sensor, a first light source of a first color, and a second light source of a second color, arranged along an expected direction of travel of an object.

BRIEF DESCRIPTION OF THE DRAWINGS

FIG. 1A is a diagram illustrating an object tracking system in accordance with a first embodiment of the present application.

FIG. 1B is a diagram illustrating an object tracking system in accordance with a second embodiment of the present application.

FIG. 2A is a diagram illustrating LED activation based on two LEDs/module in accordance with a first embodiment of the present application.

FIG. 2B is a diagram illustrating LED activation based on three LEDs/module in accordance with a second embodiment of the present application.

FIG. 3 is a diagram illustrating a stored sequence in a memory, in accordance with embodiments of the present application.

FIG. 4A is a diagram illustrating object movement that lags a recorded sequence, in accordance with embodiments of the present application.

FIG. 4B is a diagram illustrating object movement that leads a recorded sequence, in accordance with embodiments of the present application.

FIG. 4C is a diagram illustrating object movement that matches a recorded sequence, in accordance with embodiments of the present application.

FIG. 5A is a flowchart illustrating an initialization method for tracking object movement, in accordance with embodiments of the present application.

FIG. 5B is a diagram illustrating time stamp generation based on sensors, in accordance with embodiments of the present application.

FIG. 6 is a flowchart illustrating a training method for tracking object movement, in accordance with embodiments of the present application.

DETAILED DESCRIPTION

Referring now to FIG. 1A, a diagram illustrating an object tracking system 100 in accordance with a first embodiment of the present application is shown. The object tracking system 100 senses moving objects 104 using a sensor array 124. The sensor array 124 includes two or more sensors that are able to detect the moving object 104 within a sensing distance 164 of each sensor. The moving object 104 moves along a direction of travel 108 at a velocity and possibly with a positive or negative acceleration (i.e. either at a constant velocity or any combination of slowing down or speeding up). At any time, one or more sensors may detect the moving object 104 and be activated sensors 144 in response to the moving object 104 within a sensing distance 164 of the sensor. Activated sensors 144 produce active sensor outputs 136 to sensor/light source groups 132 and a processor 116. FIG. 5B shows a sensor output 136 where an object is detected for an object sense period 572. The activated sensors 144 produce an active sensor level 558 during the object sense period 572, and an inactive sensor level 554 at all other times.

The object tracking system 100 also includes an LED array 128. In the first embodiment, the LED array 128 includes a number of LED modules 228A, where each module 228A includes two LEDs. The number of LED modules 228A in the LED array 128 is the same as the number of sensors in the sensor array 124, since each sensor in the sensor array 124 is directly and permanently associated with an LED module 228A in the LED array 128. Therefore, because there are a same number of sensors in the sensor array 124 and LED modules 228A in the LED array 128, it is helpful to think of a number of sensor/light source groups 132—where each sensor/light source group 132 includes one sensor and one LED module 228A.

Each LED module 228A includes a first light source 156 and a second light source 160. Each of the two light sources 156, 160 in each LED module 228A is a different color in order to visually differentiate object 104 motion from a stored or recorded playback sequence 140. In one embodiment, the first light source 156 and the second light source 160 are LEDs. Preferably, the first light source 156 and the second light source 160 are monochromatic light sources so that when both light sources 156, 160 are simultaneously active, the colors of the two light sources are additive and form a perceived third color. For example, if the first light source 156 is red and the second light source 160 is blue 160, when both light sources 156, 160 are simultaneously active, an observer would interpret the two light sources 156, 160 as a purple color. This third color is important since it indicates synchronization between object 104 motion and playback of the stored sequence 104.

The object tracking system 100 also includes one or more object tracking devices 112. Object tracking devices 112 are computers that receive a number of sensor outputs 136 (one per each sensor) and output an equal number of first light source 156 driven signals, which collectively form the stored sequence 140. Each object tracking device 112 includes one or more processors 116 and a memory 120. The memory 120 includes one or more applications 148 and data 152.

The processor 116 executes an operating system and one or more software applications 148, which are generally stored in the memory 120. The processor 116 may include any type of processor known in the art, including embedded CPUs, RISC CPUs, Intel or Apple-compatible CPUs, and may include any combination of hardware and software. Processor 116 may include several devices including field-programmable gate arrays (FPGAs), memory controllers, North Bridge devices, and/or South Bridge devices. Although in most embodiments, processor 116 fetches application 148 program instructions and data/metadata 152 from the memory 120, it should be understood that processor 116 and applications 148 may be configured in any allowable hardware/software configuration, including pure hardware configurations implemented in ASIC or FPGA forms.

The memory 120 may include one or both of volatile and nonvolatile memory types. In some embodiments, the memory 120 include firmware which includes program instructions that processor 116 fetches and executes, including program instructions 148 for the processes disclosed herein. Examples of non-volatile memory may include, but are not limited to, flash memory, SD, Erasable Programmable Read Only Memory (EPROM), Electrically Erasable Programmable Read Only Memory (EEPROM), hard disks, and Non-Volatile Read-Only Memory (NOVRAM). Volatile memory stores various data structures and user data. Examples of volatile memory may include, but are not limited to, Static Random Access Memory (SRAM), Dual Data Rate Random Access Memory (DDR RAM), Dual Data Rate 2 Random Access Memory (DDR2 RAM), Dual Data Rate 3 Random Access Memory (DDR3 RAM), Zero Capacitor Random Access Memory (Z-RAM), Twin-Transistor Random Access Memory (TTRAM), Asynchronous Random Access Memory (A-RAM), ETA Random Access Memory (ETA RAM), and other forms of temporary memory. The memory 120 may store any combination of data/metadata 152 and one or more applications 148. Data/metadata 152 may include various data structures in support of the operating system and software applications 148. Data/metadata 152 may also include one or more stored sequences 140. In one embodiment, multiple stored sequences 140 may be present in data 152 for different moving objects 104 or types of objects 104. In another embodiment, multiple stored sequences 140 may be present in data 152 for multiple passes for a same moving object 104.

Referring now to FIG. 1B, a diagram illustrating an object tracking system 170 in accordance with a second embodiment of the present application is shown. Object tracking system 170 is similar to object tracking system 100 of FIG. 1A, but uses an LED array 174 that includes LED modules 228B having three LEDs/module instead of two LEDs/module. Three LEDs/module 228B allows the "synchronized" color to be a third LED color instead of a visual combination of the first and second colors. For example, with a red-green-blue LED module, the first light source 156 could be red, the second light source 160 could be green, and the third light source 182 could be blue. Any other combination may be possible depending on the available light source or LED colors. This embodiment has the advantage that the synchronized color may be more differentiated from a visual combination of the first and second colors, and possibly easier to detect.

The object tracking system 170 drives the first light sources 156 with the stored sequence playback 140 and the second light sources 160 from the sensor outputs 136, but drives the third light sources 182 from a logical AND (AND logic 178) of each of the stored sequence 140 and corresponding sensor output 136. In this way, for a given sensor/light source group 132, the third light source 182 is illuminated whenever both the first light source 156 and second light source 160 are simultaneously illuminated. AND logic 178 may be implemented in any form that provides the required AND function, including but not limited to hardware AND gates in logic, or an AND instruction within applications 148 and executed by the processor 116.

Referring now to FIG. 2A, a diagram illustrating LED activation based on two LEDs/module 200, in accordance with a first embodiment of the present application is shown. The first embodiment, also reflected in FIG. 1A, may utilize two LED modules 228A to provide the light sources 156, 160. It may also utilize discrete LEDs or light sources 156, 160 and it should be recognized that LED modules 228A simply provide a more compact and preferred arrangement over other possible alternatives.

Each two LED module 228A may be directly coupled to an appropriate DC voltage in order to provide power to activate a $1^{st}$ color LED 204 and a 2nd color LED 208, where the two LED module 228A includes the $1^{st}$ color LED 204 and the 2nd color LED 208. The $1^{st}$ color LED 204 may be connected to a current-limiting resistor 224A, which is in turn connected to a FET (FET1 220A) as shown. The 2nd color LED 208 may be connected to a current-limiting resistor 224B, which is in turn connected to a FET (FET2 220B) as shown. FET1 220A may be connected to an output general purpose I/O (GPIO) pin 216 of the processor 116, which drives the GPIO signal 216 as part of the stored sequence 140. FET2 220B may be connected to a sensor output 212, which corresponds to one of the sensor outputs 136 shown in FIGS. 1A and 1B. When the corresponding GPIO 216 is driven by the processor 116, FET1 220A drives the first color LED 204 and illuminates the $1^{st}$ color LED 204. When the corresponding sensor output 212 is driven by the sensor outputs 136, FET2 220B drives the $2^{nd}$ color LED 208 and illuminates the $2^{nd}$ color LED 208.

Referring now to FIG. 2B, a diagram illustrating LED activation based on three LEDs/module, in accordance with a second embodiment of the present application is shown. The second embodiment, also reflected in FIG. 1B, may utilize three LED modules 228B to provide the light sources 156, 160. It may also utilize discrete LEDs or light sources 156, 160, 182 and it should be recognized that LED modules 228B simply provide a more compact and preferred arrangement over other possible alternatives.

Each three LED module 228B may be directly coupled to an appropriate DC voltage in order to provide power to activate a $1^{st}$ color LED 204 and a 2nd color LED 208, where the three LED module 228B includes the $1^{st}$ color LED 204, the 2nd color LED 208, and a $3^{rd}$ color LED 254. The $1^{st}$ color LED 204 may be connected to a current-limiting resistor 224A, which is in turn connected to a FET (FET1 220A) as shown. The 2nd color LED 208 may be connected to a current-limiting resistor 224B, which is in turn connected to a FET (FET2 220B) as shown. The $3^{rd}$ color LED 254 may be connected to a current-limiting resistor 224C, which is in turn connected to a FET (FET3 220C) as shown.

FET1 220A may be connected to an output general purpose I/O (GPIO) pin 216 of the processor 116, which drives the GPIO signal 216 as part of the stored sequence 140. FET2 220B may be connected to a sensor output 212, which corresponds to one of the sensor outputs 136 shown in FIGS. 1A and 1B. FET2 220C may be connected to an AND gate 258 output, which drives FET 3 220C if sensor output 212 and stored sequence playback 216 are simultaneously active. When the corresponding GPIO 216 is driven by the processor 216, FET1 220A drives the first color LED 204 and illuminates the $1^{st}$ color LED 204. When the corresponding sensor output 212 is driven by the sensor outputs 136, FET2 220B drives the $2^{nd}$ color LED 208 and illuminates the $2^{nd}$ color LED 208. When both the $1^{st}$ color LED 204 and the $2^{nd}$ color LED 208 are simultaneously illuminated, the $3^{rd}$ color LED 254 will also be illuminated, indicating a synchronized state between the playback sequence 140 and the moving object 104.

Referring now to FIG. 3, a diagram illustrating a stored sequence in a memory 152, in accordance with embodiments of the present application. The stored sequence drives stored sequence playback 140 to the $1^{st}$, $2^{nd}$, or $3^{rd}$ light sources 156, 160, 182 of the LED array 128, 174. There are a number of entries 316 stored in a data portion 152 of the memory 120, where each entry 316 includes the information needed by the processor 116 in order to illuminate a specific light source 156, 160, 182 or LED 204, 208, 254. Each entry 316 includes a sensor/light group identifier 304, which uniquely identifies which sensor/light source group 132 is affected by the current entry 316. Each entry 316 may also include a starting time stamp 308 and an ending time stamp 312, which define the specific time that a specific light source 156, 160, 182 or LED 204, 208, 254 is illuminated. The difference in time between a starting time stamp 308 and an ending time stamp 312 is the duration for illumination or object sense period 572.

There are N entries within the stored sequence, where the number of entries in the stored sequence is the same as the number of sensor/light source groups 320. The stored sequence may be executed in a consecutive order by the processor, such as 304A/308A/312A, then 304B/308B/

312B, then 304C/308C/312C, and so on until 304N, 308N, 312N is reached. However, the time stamps 308, 312 of different entries 316 may well overlap in time, which may result in multiple light sources 156, 160, 182 or LEDs 204, 208, 254 being simultaneously illuminated. This may be visually advantageous, as it will display a smooth continuous stream of light rather than discrete illuminations with no overlap, which may appear irregular or jerky. In most embodiments, a given sensor/light source group 132 is represented only one time within a given stored sequence. Additionally (but not necessarily), the sensor/light source group identifiers 304 in most cases represent consecutively positioned sensor/light source groups 132.

Referring now to FIG. 4A, a diagram illustrating object movement that lags a recorded sequence 400, in accordance with embodiments of the present application is shown. The moving object 104 may precede, be in synchronization with, or lag a stored sequence playback 140 corresponding to a recorded sequence 404. If the moving object 104 lags the recorded sequence 404, then the first light source 156 or $1^{st}$ color LED 204 will be lit in the direction of travel before the second light source 160 or $2^{nd}$ color LED 208. The visual appearance 408 will be the first color 412 "leading" in the direction of travel 108. This appearance 408 corresponds to a moving object 104 either moving too slow compared to the recorded sequence 404 or the moving object 104 started moving too late.

Referring now to FIG. 4B, a diagram illustrating object movement that leads a recorded sequence 430, in accordance with embodiments of the present application is shown. If the moving object 104 leads the recorded sequence 404, then the second light source 160 or 2nd color LED 208 will be lit in the direction of travel before the first light source 156 or 1st color LED 204. The visual appearance 408 will be the second color 416 "leading" in the direction of travel 108. This appearance 408 corresponds to a moving object 104 either moving too fast compared to the recorded sequence 404 or the moving object 104 started moving too early.

Referring now to FIG. 4C, a diagram illustrating object movement that matches a recorded sequence 460, in accordance with embodiments of the present application is shown. If the moving object 104 matches the recorded sequence 404, then the first light source 156 or 1st color LED 204 will be illuminated at the same time as the second light source 160 or 2nd color LED 208 in the direction of travel 108. The visual appearance 408 will be a $3^{rd}$ color or white leading in the direction of travel 108. This visual appearance 408 corresponds to a moving object 104 moving at the same velocity and acceleration as the recorded sequence 404, which generally indicates a successful training or learning iteration.

Referring now to FIG. 5A, a flowchart illustrating an initialization method for tracking object movement 500, in accordance with embodiments of the present application is shown. Flow begins at block 504.

At block 504, a tracking device is initialized. Tracking device initialization may include preparing or cueing the processor 116 to begin a new elapsed time sequence. The time sequence may be initiated by a control activation (a start button or other physical or virtual control) or by the object 104 either initiating its own movement or the object 104 moving past an established start point. Flow proceeds to blocks 508 and 512.

At block 508, the training object is moved at a desired velocity and acceleration in a direction of movement 108. Flow proceeds to block 516.

At block 512, time stamps 308, 312 and sensor/LED group IDs 304 for activated sensors 144 are stored. This creates an entry data structure 316 in memory 152 similar to what is shown in FIG. 3. In one embodiment, the memory 152 includes a series of data structures for several trial runs. In one embodiment, a user selects one of the saved data structures from two or more saved data structures. Flow proceeds to block 516.

At block 516, the training object is no longer tracked. In one embodiment, there are no activated sensors 144 and no sensors detecting the object 104. In another embodiment, the moving object 104 has moved past the object tracking system 100, 170, and is no longer able to be tracked. Flow ends at block 516.

Referring now to FIG. 5B, a diagram illustrating time stamp generation based on sensors 550, in accordance with embodiments of the present application is shown. FIG. 5B shows a graph where the vertical axis represents a level of a sensor output 136 and the horizontal axis is time 562. When a sensor is not detecting an object 104, the sensor output 136 reflects an inactive sensor level 554. When the sensor is detecting an object 104, the sensor output 136 reflects an active sensor level 558. In the embodiment illustrated, the sensor may be configured to provide an active-low sensor output 136. In another embodiment, the sensor is configured to provide an active-high sensor output 136.

When the sensor initially detects an object 104, a first time stamp 564 may be produced and stored as a starting time stamp 308. The object is thereafter sensed for an object sense period 572, at the conclusion of which the object 104 is no longer sensed. A second time stamp 568 is produced and stored at the end of the object sense period 572.

Referring now to FIG. 6, a flowchart illustrating a training method for tracking object movement 600, in accordance with embodiments of the present application is shown. Flow begins at block 604.

At block 604, a tracking device 112 is initialized. A recorded sequence 404 in memory 152 is identified. Flow proceeds to block 608.

At block 608, stored time stamps 308, 312 and sensor/group IDs 304 for activated sensors 144 are retrieved. The processor 116 retrieves the stored time stamps 308, 312 and sensor/group IDs 304 from memory 152. Flow proceeds to block 612.

At block 612, the start of playback for retrieved time stamps 308, 312 is synchronized with the start of object movement 104 or a control activation. In one embodiment, sensors detect a start of object movement 104 and the start of playback of retrieved time stamps 308, 312 is synchronized with the detected movement 104. This mode may be useful for a student using the apparatus in a self-training mode. The playback of time stamps 308, 312 may occur at the same time as detected object movement 104 or any time delay after the detected movement 104. In another embodiment, sensors detect a control activation and the start of playback of retrieved time stamps 308, 312 is synchronized with the control activation. For example, pushing a push-button control may initiate playback of retrieved time stamps 308, 312. This mode may be useful for a cued start by an instructor.

At block 616, first light sources 156 or LEDs 204 that correspond to the retrieved time stamps 308, 312 are activated. Because the first light sources 156 or LEDs 204 are activated based on the retrieved time stamps 308, 312, the illumination of the first light sources 156 or LEDs 404 is absolutely predictable and known. The first light sources 156 or LEDs 204 form the reference. Flow ends at block 616.

At block 620, second light sources 160 or LEDs 208 that correspond to sensed object movement 104 are activated. Because the second light sources 160 or LEDs 208 are activated based on the sensed object movement 104, the illumination of the second light sources 160 or LEDs 208 is unpredictable and unknown. Flow proceeds to optional block 624.

At optional block 624, actual time stamps 308, 312 are recorded as the object is moved 104. Flow ends at optional block 624.

Finally, those skilled in the art should appreciate that they can readily use the disclosed conception and specific embodiments as a basis for designing or modifying other structures for carrying out the same purposes of the present application without departing from the spirit and scope of the application as defined by the appended claims.

It will be readily understood that the components of the application, as generally described and illustrated in the figures herein, may be arranged and designed in a wide variety of different configurations. Thus, the detailed description of the embodiments is not intended to limit the scope of the application as claimed, but is merely representative of selected and exemplary embodiments of the application.

One having ordinary skill in the art will readily understand that the application as discussed above may be practiced with steps in a different order, and/or with hardware elements in configurations that are different than those which are specifically disclosed. Therefore, although the application has been described based upon these preferred embodiments, it would be apparent to those of skill in the art that certain modifications, variations, and alternative constructions would be apparent, while remaining within the spirit and scope of the application. In order to determine the metes and bounds of the application, therefore, reference should be made to the present claims.

While preferred embodiments of the present application have been described, it is to be understood that the embodiments described are illustrative only and the scope of the application is to be defined solely by the appended claims when considered with a full range of equivalents and modifications (e.g., protocols, hardware devices, software platforms etc.) thereto.

I claim:

1. A device comprising:
   a plurality of sensor/light source groups, each comprising a sensor, a first light source of a first color, and a second light source of a second color, arranged in sequence along an expected direction of travel of an object;
   a device to track objects, coupled to the plurality of sensor/light source groups, configured to:
      drive first light sources in response to playback of a stored sequence comprising a plurality of entries, each entry comprising:
         a sensor/light source group identifier;
         a start time stamp that identifies a start time to turn on a first light source that corresponds to the entry; and
         an end time stamp to turn off the first light source that corresponds to the entry; and
      drive second light sources in response to received active sensor outputs from sensors of the plurality of sensor/light source groups.

2. The device of claim 1, wherein each sensor produces an active sensor output in response to the object within a sensed distance from the sensor.

3. The device of claim 1, wherein simultaneously illuminated first and second light sources of a sensor/light source group indicates object travel matches the stored sequence, wherein simultaneously illuminated first and second light sources produces a third color different than the first and second colors.

4. The device of claim 1, wherein the stored sequence identifies a desired illumination time sequence for first light sources, the stored sequence comprising a number of entries that corresponds to a number of sensor/light source groups in the plurality of sensor/light source groups.

5. The device of claim 4, wherein the device to track objects coordinates playback of the stored sequence with detected object movement from a start position.

6. The device of claim 1, wherein each sensor/light source group comprises a third light source, the third light source configured to illuminate in response to the first and second light sources of the same sensor/light source group are illuminated.

7. A system, comprising:
   an object in motion;
   a plurality of sensor/light source groups, each comprising:
      a sensor;
      a first light source in a first color; and
      a second light source in a second color; and
   a device to track objects, coupled to the plurality of sensor/light source groups, comprising:
      a processor; and
      a memory, coupled to the processor, comprising:
         instructions; and
         a stored sequence comprising a plurality of entries, each entry comprising:
            a sensor/light source group identifier;
            a start time stamp that identifies a start time to turn on a first light source that corresponds to the entry; and
            an end time stamp to turn off the first light source that corresponds to the entry;
      the processor configured to execute the instructions to:
         drive first light sources in response to playback of the stored sequence; and
         drive second light sources in response to received active sensor outputs from sensors of the plurality of sensor/light source groups.

8. The system of claim 7, wherein each sensor produces an active sensor output in response to the object within a sensed distance from the sensor.

9. The system of claim 7, wherein simultaneously illuminated first and second light sources of a sensor/light source group indicates object motion coincides with stored sequence, wherein simultaneously illuminated first and second light sources produces a third color different than the first and second colors.

10. The system of claim 7, wherein the stored sequence is modified to match illumination times for the second light sources.

11. The system of claim 7, wherein the device to track objects coordinates playback of the stored sequence with one of detected object movement from a start position and activation of a control.

12. The system of claim 7, wherein each sensor/light source group comprises a third light source, the third light source configured to illuminate in response to the first and second light source of the same sensor light source group are illuminated.

13. The system of claim 12, wherein the device to track objects does not solely control illumination of any third light source.

14. A method, comprising:
  initiating playback of a stored sequence controlling timed sequential illumination of first light sources of a plurality of sensor/light source groups, each sensor/light source group comprising a sensor, a first light source of a first color, and a second light source of a second color, arranged along an expected direction of travel of an object, the stored sequence comprising a plurality of entries, each entry comprising:
    a sensor/light source group identifier;
    a start time stamp that identifies a start time to turn on a first light source that corresponds to the entry; and
    an end time stamp to turn off the first light source that corresponds to the entry;
  illuminating first light sources as directed by playback of the stored sequence;
  detecting motion of the object by one or more sensors;
  illuminating second light sources in response to corresponding sensors of the one or more sensors detecting the object; and
  detecting a third color in response to illuminating the first and second light sources in one or more sensor/light source groups.

15. The method of claim 14, wherein initiating playback of the stored sequence comprising one of:
  coordinating playback with detected object movement from a start position; and
  activating a control.

16. The method of claim 14, wherein each sensor/light source group comprising a third light source, the third light source configured to illuminate in response to simultaneously illuminating the first and second light source of the same sensor light source group.

17. The method of claim 14, further comprising:
  producing active sensor outputs from the sensors in response to the object within a detection range of the sensors.

18. The method of claim 14, further comprising:
  creating the stored sequence in response to a previous object motion.

19. The method of claim 14, further wherein the stored sequence identifying a desired illumination timing of first light sources.

* * * * *